United States Patent
Liprie et al.

(10) Patent No.: US 6,508,754 B1
(45) Date of Patent: Jan. 21, 2003

(54) SOURCE WIRE FOR RADIATION TREATMENT

(75) Inventors: Sam F. Liprie, Lake Charles, LA (US); Lisa D. Futato, Barrington, RI (US); James Correia, Seymour, CT (US); Stanislaw Kostrzewski, Newton, CT (US)

(73) Assignee: Interventional Therapies, Westport, CT (US)

( * ) Notice: Subject to any disclaimer, the term of this patent is extended or adjusted under 35 U.S.C. 154(b) by 0 days.

(21) Appl. No.: 09/509,313
(22) PCT Filed: Sep. 23, 1998
(86) PCT No.: PCT/US98/19819
§ 371 (c)(1), (2), (4) Date: Sep. 22, 2000
(87) PCT Pub. No.: WO99/15234
PCT Pub. Date: Apr. 1, 1999

Related U.S. Application Data
(60) Provisional application No. 60/059,601, filed on Sep. 23, 1997.

(51) Int. Cl.[7] ............ A61N 5/00; A61M 36/00; A61B 6/00
(52) U.S. Cl. ............... 600/3; 600/7; 600/434
(58) Field of Search ............... 600/3, 7, 434; 252/649

(56) References Cited

U.S. PATENT DOCUMENTS

| | | | |
|---|---|---|---|
| 857,992 A | 6/1907 | Gilchrist | |
| 1,753,287 A | 4/1930 | Failla | |
| 1,954,868 A | 4/1934 | Failla et al. | 174/177 |
| 2,546,761 A | 3/1951 | Loftus | 128/1.2 |
| 2,738,294 A | 3/1956 | Spence | 134/42 |
| 2,768,271 A | 10/1956 | Meredith | 219/85 |
| 3,351,049 A | 11/1967 | Lawrence | 128/1.2 |
| 3,558,369 A | 1/1971 | Wang et al. | 148/11.5 |
| 3,567,943 A | 3/1971 | Wallhausen et al. | 250/106 |
| 3,605,725 A | 9/1971 | Bentov | 128/2.05 |
| 3,620,212 A | 11/1971 | Fannon et al. | 128/130 |
| 3,674,006 A | 7/1972 | Holmer | 128/1.2 |

(List continued on next page.)

FOREIGN PATENT DOCUMENTS

| | | |
|---|---|---|
| EP | 0 145 166 A3 | 6/1985 |
| EP | 0 199 715 A2 | 10/1986 |

(List continued on next page.)

OTHER PUBLICATIONS

Jani, Shirish K. et al., "Best: Manually Loaded Iridium 192 Ribbon", From Waksman R (ED). Vascular Brachythrapy, Second Edition. Armonk, NY: Futura Publishing Company, Inc. 1999 pp. 485–488.

(List continued on next page.)

Primary Examiner—Kevin Shaver
Assistant Examiner—Nikita R Veniaminov
(74) Attorney, Agent, or Firm—Cantor Colburn LLP

(57) ABSTRACT

A source wire for radiation treatment of diseases is provided, comprising a relatively long elongate flexible wire having a proximal end and a distal end, the distal end of the wire having a wire end face substantially perpendicular to a longitudinal axis of the wire; a relatively short flexible tube having a proximal end and a distal end, the distal end of the tube being sealed, the tube having a tube end face at the proximal end and substantially perpendicular to the distal wire end face of the wire, the tube having an inner diameter defining a cavity; and a core capable of being irradiated to form at least one radioactive source positioned within the cavity.

22 Claims, 11 Drawing Sheets

U.S. PATENT DOCUMENTS

| | | | | |
|---|---|---|---|---|
| 3,890,977 A | 6/1975 | Wilson | | 128/418 |
| 3,953,253 A | 4/1976 | Clark | | 148/131 |
| 4,037,324 A | 7/1977 | Andreasen | | 32/14 A |
| 4,069,226 A | 1/1978 | Kablaoui et al. | | 260/307 F |
| 4,233,690 A | 11/1980 | Akins | | 3/1.5 |
| 4,283,233 A | 8/1981 | Goldstein et al. | | 148/11.5 R |
| 4,304,613 A | 12/1981 | Wang et al. | | 148/11.5 N |
| 4,385,635 A | 5/1983 | Ruiz | | 128/658 |
| 4,411,655 A | 10/1983 | Schreck | | 604/165 |
| 4,425,908 A | 1/1984 | Simon | | 128/1 R |
| 4,427,000 A | 1/1984 | Ueda | | 128/6 |
| 4,503,569 A | 3/1985 | Dotter | | 3/1.4 |
| 4,505,767 A | 3/1985 | Quin | | 148/402 |
| 4,512,338 A | 4/1985 | Balko et al. | | 128/1 R |
| 4,538,622 A | 9/1985 | Samson et al. | | 128/772 |
| 4,554,929 A | 11/1985 | Samson et al. | | 128/772 |
| 4,580,568 A | 4/1986 | Gianturco | | 128/345 |
| 4,665,906 A | 5/1987 | Jervis | | 128/92 YN |
| 4,702,228 A | 10/1987 | Russell, Jr. et al. | | 128/1.2 |
| 4,763,642 A | 8/1988 | Horowitz | | 128/1.2 |
| 4,768,507 A | 9/1988 | Fischell et al. | | 128/303 R |
| 4,776,844 A | 10/1988 | Ueda | | 604/95 |
| 4,815,449 A | 3/1989 | Horowitz | | 600/7 |
| 4,827,941 A | 5/1989 | Taylor et al. | | 128/657 |
| 4,846,573 A | 7/1989 | Taylor et al. | | 356/241 |
| 4,861,520 A | * 8/1989 | van't Hooft et al. | | 252/644 |
| 4,875,489 A | 10/1989 | Messner et al. | | 128/772 |
| 4,881,981 A | 11/1989 | Thoma et al. | | 148/11.5 R |
| 4,891,165 A | 1/1990 | Suthanthiran | | 252/633 |
| 4,925,445 A | 5/1990 | Sakamoto et al. | | 604/95 |
| 4,935,068 A | 6/1990 | Duerig | | 148/11.5 C |
| 4,943,326 A | 7/1990 | Ozawa et al. | | 148/11.5 N |
| 4,984,581 A | 1/1991 | Stice | | 128/772 |
| 4,991,602 A | 2/1991 | Amplatz et al. | | 128/772 |
| 5,001,446 A | 3/1991 | Tsuji et al. | | 335/43 |
| 5,025,799 A | 6/1991 | Wilson | | 128/772 |
| 5,059,166 A | 10/1991 | Fischell et al. | | 600/3 |
| 5,067,489 A | 11/1991 | Lind | | 128/772 |
| 5,067,957 A | 11/1991 | Jervis | | 606/108 |
| 5,069,226 A | 12/1991 | Yamauchi et al. | | 128/772 |
| 5,084,002 A | * 1/1992 | Liprie | | 600/7 |
| 5,117,838 A | 6/1992 | Palmer et al. | | 128/772 |
| 5,120,308 A | 6/1992 | Hess | | 604/95 |
| 5,141,487 A | 8/1992 | Liprie | | 600/7 |
| 5,143,085 A | 9/1992 | Wilson | | 128/772 |
| 5,147,282 A | 9/1992 | Kan | | 600/1 |
| 5,163,896 A | 11/1992 | Suthanthiran et al. | | 600/8 |
| 5,188,111 A | * 2/1993 | Yates et al. | | 600/434 |
| 5,188,621 A | 2/1993 | Samson | | 604/264 |
| 5,230,348 A | 7/1993 | Ishibe et al. | | 128/772 |
| 5,238,004 A | 8/1993 | Sahatjian et al. | | 128/772 |
| 5,243,996 A | 9/1993 | Hall | | 128/772 |
| 5,282,781 A | * 2/1994 | Liprie | | 600/3 |
| 5,302,168 A | 4/1994 | Hess | | 600/3 |
| 5,318,527 A | 6/1994 | Hyde et al. | | 604/95 |
| 5,322,499 A | 6/1994 | Liprie | | 600/8 |
| 5,341,818 A | 8/1994 | Abrams et al. | | 128/772 |
| 5,342,283 A | 8/1994 | Good | | 600/8 |
| 5,368,049 A | 11/1994 | Raman et al. | | 128/772 |
| 5,395,300 A | * 3/1995 | Liprie | | 600/3 |
| 5,411,466 A | 5/1995 | Hess | | 600/3 |
| 5,411,476 A | 5/1995 | Abrams et al. | | 604/95 |
| 5,454,794 A | 10/1995 | Narciso et al. | | 604/280 |
| 5,503,613 A | 4/1996 | Weinberger | | 600/3 |
| 5,503,614 A | 4/1996 | Liprie | | 600/7 |
| 5,514,115 A | 5/1996 | Frantzen et al. | | 604/281 |
| 5,637,089 A | 6/1997 | Abrams et al. | | 604/95 |
| 5,713,828 A | * 2/1998 | Coniglione | | 600/7 |
| 5,782,741 A | * 7/1998 | Brawdshaw et al. | | 600/3 |
| 5,833,593 A | 11/1998 | Liprie | | 600/3 |
| 5,857,956 A | 1/1999 | Liprie | | 600/7 |
| 5,871,436 A | 2/1999 | Eury | | 600/3 |
| 5,873,811 A | 2/1999 | Wang et al. | | 600/5 |
| 5,924,974 A | 7/1999 | Loffler | | 600/3 |
| 5,925,353 A | 7/1999 | Mosseri | | 424/178.1 |
| 6,077,298 A | 6/2000 | Tu et al. | | 623/1.19 |
| 6,165,292 A | 12/2000 | Abrams et al. | | 148/563 |
| 6,248,082 B1 | 6/2001 | Jafari | | 600/585 |
| 6,283,910 B1 | 9/2001 | Bradshaw et al. | | |

FOREIGN PATENT DOCUMENTS

| | | |
|---|---|---|
| EP | 0 340 304 A1 | 11/1989 |
| EP | 0 395 098 A1 | 10/1990 |
| EP | 0 480 427 A1 | 4/1992 |
| EP | 0 491 349 A2 | 6/1992 |
| EP | 0 491 349 A3 | 6/1992 |
| EP | 0 491 349 B1 | 6/1992 |
| EP | 0 515 078 A2 | 11/1992 |
| EP | 0 550 258 A1 | 7/1993 |
| EP | 0 569 166 A1 | 11/1993 |
| JP | 50-19512 | 3/1975 |
| JP | 62-199757 | 9/1987 |
| JP | 6-21469 | 1/1994 |
| JP | 6-140410 | 5/1994 |
| WO | WO 89/10088 | 11/1989 |
| WO | WO 90/13329 | 11/1990 |
| WO | WO 91/15152 | 10/1991 |
| WO | WO 93/04735 | 3/1993 |
| WO | WO 94/23789 | 10/1994 |
| WO | WO 94/25106 | 11/1994 |

OTHER PUBLICATIONS

Hillstead, Richard A. Noveste Beta–Cath Intracoronary Beta Radiation System, From Waksman R. (ED0. Vascular Brachytherapy, Second Edition. Armonk, N.Y.: Futura Publishing Co. Inc. 1999, pp. 489–497.

Bottcher, H.D. et al, Endovascular Irradiation—A New Method to Avoid Recurrent Stenosis After Stent Implantation in Peripheral Arteries: Technique and Preliminary Results, Int. J. Radiation Oncology Biol. Phys. vol. 29, No. 1, pp. 183–186.

Dyke, Van et al., Cardiac Catheterization Using a Radioactive Catheter and Scintillation Camera, Radiology 91: 749–752. Oct. 1968.

Faxon, D. et al, The Angiorad Gamma Wire System, Waksman R (ED). Vascular Brachytherapy, Second Edition. Armonk, NY. Futura Publishing Co. Inc, 1999, pp. 553–559.

Verin, Vitali, M.D., et al. Clinical Trials Using Beta Energy Radiation: Experimental and Clinical Experience with Schneider–Sauerwin Intravascular Radiation System, from Waksmanr (ED). Vascular Brachytherapy, Second Edition. Armonk, NY: Futura Publishing Company, Inc. 1999, pp. 537–551.

Loffler, E.G. et al, Nucletron Afterloading Technology for Brachytherapy: The Peripheral System: From Waksman R (ED). Vascular Brachytherapy, Second Edition. Armonk, NY.: Futura Publishing Co. Inc, 1999 pp. 499–504.

Raizner, et al. "The Guidant Coronary Source Wire System," from Waksman, R. (ED) Vascular Brachytherapy, Second Edition. Armonk, N.Y.: Futura Publishing Company, Inc., 1999, pp. 505–519.

Freidman, Myer, et al. "Effect of Iridium 192 Radiation on Thromboatherosclerotic Plaque in the Rabbit Aorta", Arch Path–vol. 80, pp. 285–290, Sep. 1965.

Weinberger, et al. Use of Liquid–Filled Balloons for Coronary Irradiation, From Waksman R (ED). Vascular Brachytherapy, Second Edition. Armonk, NY.: Futura Publishing Co. Inc. 1999, pp. 521–526.

Chornenky, "Intravascular Soft X–Ray Therapy", from Waksman, R. (ED) Vascular Brachytherapy, Second Edition, Armonk, NY: Futura Publishing Co., Inc., 1999 pp. 561–567.

Apple, et al. "Xenon 133 Gas–Filled Balloon", from Waksman R. (ED) Vascular Brachytherapy, Second Edition, Armonk NY: Futura Publishing Co, Inc. 1999, pp. 569–578.

Bass, Radiation Safety Requirements for Vascular Radiotherapy in the Catheterization Laboratory, from Waksman R. (ED), Vascular Brachytherapy, Second Edition. Armonk, N.Y.: Futura Publishing Co, Inc. 1999, pp. 581–592.

Ryan, Regulatory Considerations for Approval of Vascular Radiation Studies in the United States, from Waksman R (ED) Vascular Brachytherapy, Second Edition. Armonk, NY: Futura Publishing Co. Inc. 1999 pp. 593–599.

Weinstraub, "The Economics of Brachytherapy", from Waksman R (ED) Vascular Brachytherapy, Second Edition. Armonk, NY: Futura Publishing Co., Inc. 1999 pp. 601–611.

* cited by examiner

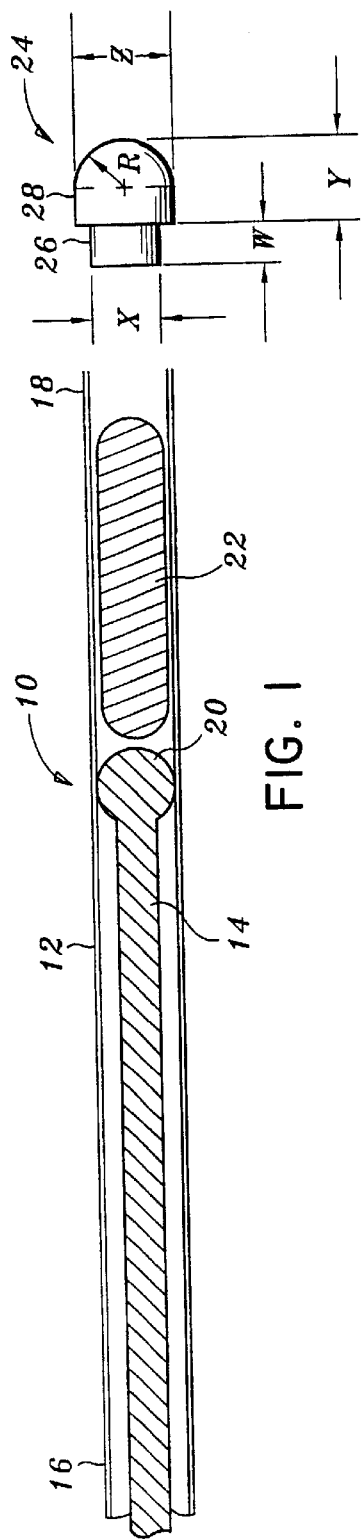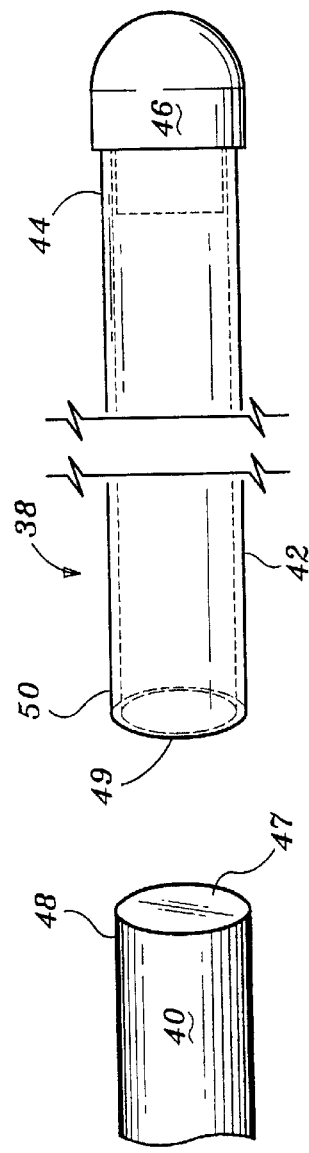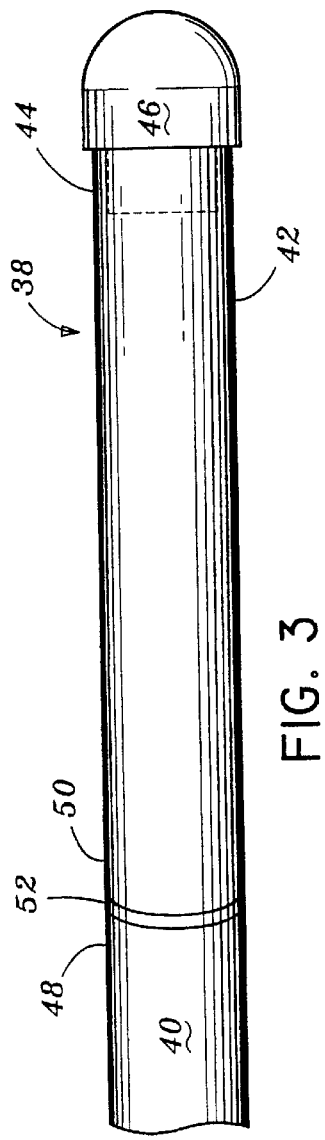

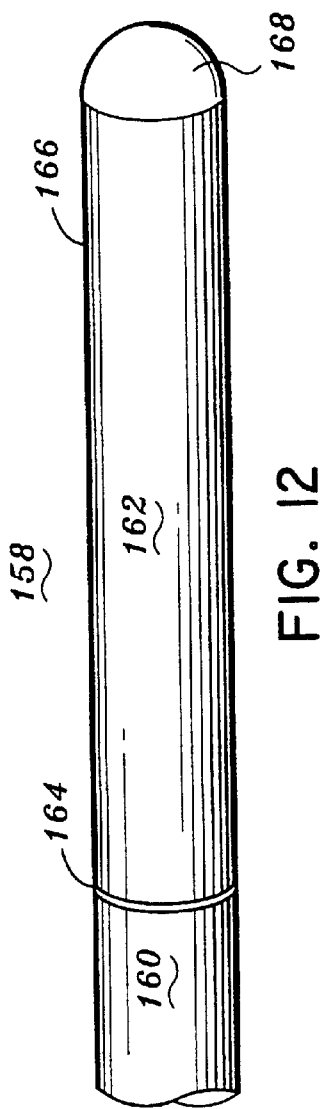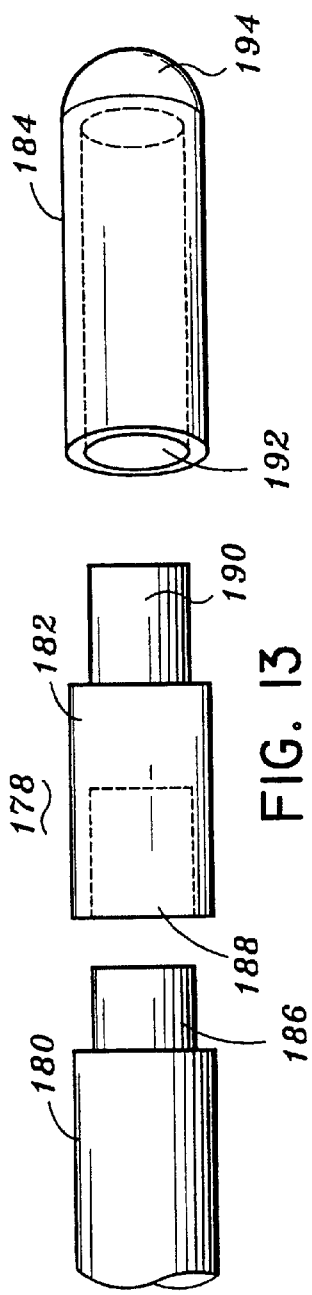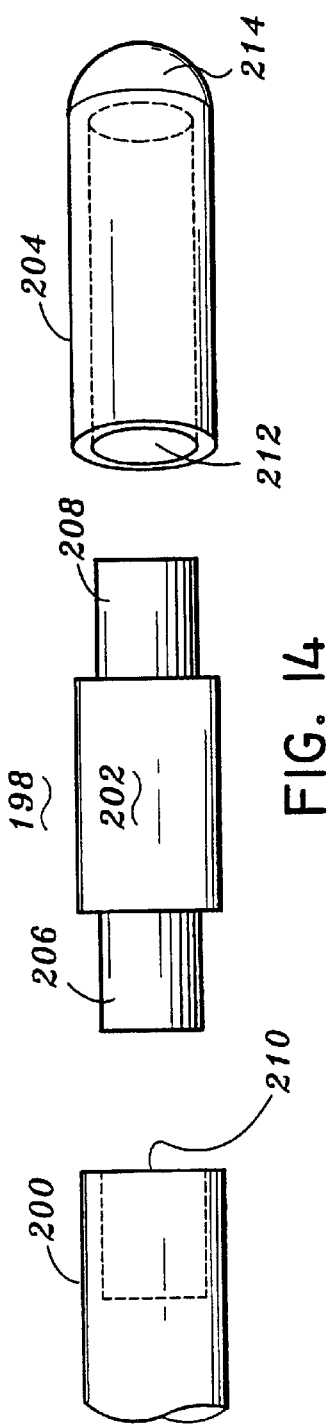

SOURCE WIRE FOR RADIATION TREATMENT

CROSS-REFERENCE TO RELATED APPLICATION

This application claims priority to U.S. Provisional Application Serial No. 60/059,601 filed Sep. 23, 1997, entitled, "Sourcewire for Radiation Treatment", the entire contents of which are incorporated herein by reference.

BACKGROUND

1. Technical Field

Technical field relates generally to radioactive sourcewires for treatment of diseases, and, more particularly, to a flexible sourcewire for use in radiation therapy after an angioplasty procedure in order to minimize the occurrence of restenosis.

2. Description of the Related Art

During or after the performance of a percutaneous transluminal angioplasty procedure to relieve a constriction within a patient's vessel, it has been found beneficial to irradiate the site of the constriction to prevent reclosure or restenosis due to smooth muscle cell proliferation. Typically, a catheter having a blind lumen extending to a distal end thereof is advanced to the treatment site and a sourcewire having a radioactive tip is advanced to the treatment zone of the catheter adjacent the treatment site within the vessel. This is typically accomplished by connecting a proximal end of a catheter to a mechanism for advancing the sourcewire, such as an afterloader, and operating the afterloader to advance the sourcewire to the treatment site.

Commonly, in afterloaders, the sourcewire is substantially wound about a reel or spool with only the distal end, that containing the radioactive source, left in a straight or uncoiled position. The radioactive source is typically housed within a shielded container provided on the afterloader. In operating the afterloader, the sourcewire is unraveled off the reel and advanced through the catheter down the various narrow or tortuous pathways to reach the arteries and, in particular, the remote coronary arteries. Sourcewires may be repeatedly used over again until such time as the radioactive level of the radioactive source is of no further beneficial use.

During the repeated cycling of the sourcewire about the reel and through the catheter to reach the coronary arteries, the sourcewire is subjected to various stresses and strains along its length thereof. This may pose problems in particular sourcewire constructions which can result in cracking, buckling or kinking at various positions along the sourcewire. In one known sourcewire construction, the sourcewires are formed by having a full length tube with a substantially full length backbone wire affixed therein. The backbone wire terminates short of the distal end of the tube to define a cavity for receipt of a radioactive source or sources therein. The backbone wire construction of the radioactive sourcewire provides the advantage of allowing a relatively long treatment zone to be provided by the tube defining the cavity at a distal end thereof. Alternatively, sourcewires formed from an entirely solid wire having a drilled distal end for receipt of a radioactive core are known. The solid wire construction is less prone to damage from repeated cycling. However, when constructing sourcewires of relatively small diameters, less than 0.014 of an inch, it becomes difficult to drill a cavity into this sourcewire of sufficient length to accommodate the desired longer radioactive sources.

Thus, there exists a need for a radioactive sourcewire combining the strength and flexibility of a substantially solid wire along the predominant length thereof as well as having a tubular construction at a distalmost end to accommodate varying lengths of radioactive sources.

SUMMARY

There is provided a radioactive sourcewire having an elongated flexible and substantially solid wire and a tube extending from a distal end of the wire. A radioactive source may be provided in the cavity defined by the tube and the distal end of the tube sealed to prevent release of the radioactive source. Preferably, both the wire and tube are formed of a shaped memory alloy such as a nickel titanium alloy tor increased flexibility. Various embodiments and methods relating to the juncture of the solid wire and tube are disclosed herein. In the disclosed embodiments, the wire is formed with a flush distal face which is substantially perpendicular to longitudinal axis of the wire. Similarly, the tube is formed with a flush proximal face which is substantially perpendicular to the longitudinal axis of the tube. Various constructions are provided wherein the flush face of the wire is abutted against the flush face of the tube and the two are permanently affixed or secured together.

In a first embodiment, the wire is affixed to the tube by bringing the two flush bases into abutting relationship and providing a circumferential weld or other means of affixing the wire to the tube. The tube may then be sealed at the distal end by means of a plug affixed thereto or the distal end of the tube, as will be common in all embodiments, may be ground flush or welded closed and then ground to provide a smooth surface.

In an alternative embodiment, a connector or rod is formed projecting from the distal flush face of the wire and is configured to frictionally engage the interior of the tube. The rod does not extend the full length of the tube but terminates short of the distal end of the tube to provide a cavity for receipt of the radioactive material.

In a further alternative embodiment, a rod is initially inserted into the tube to provide a substantially flush face across the proximal end of the tube. The flush face of the proximal end of the tube is then mated as above with the flush face of the wire and the two secured by known methods.

In yet a further alternative embodiment of the disclosed sourcewire, the distal end face of the wire is drilled to form a bore for receipt of one end of the rod. As with the above embodiment, the distal end of the rod is inserted into the proximal end of the tube and the entire assembly is welded together.

Notably, where the tube is to be of a length greater than approximately 3 centimeters and less than approximately 20 centimeters, the rod may extend a significant distance into the tube. The rod may be tapered to provide flexibility along its length within the tube and include a rounded distal end which substantially seals the tube. The radioactive source would be provided distal of the rounded end and the distal end of the tube sealed as with other embodiments.

In a further alternative embodiment, a proximal end of the tube is welded shut and then ground shut, providing a flush face for abutment and a fixation to the flush surface of the wire. This provides an added advantage in assuring some structural rigidity to the proximal end of the tube when it is mated to the wire without the use of connectors. In further alternative embodiments, intermediate connectors may be provided between the wire and the tube. Specifically, the connectors may include male/female ends for receipt of a ground down male end of the wire and insertion into the female end of the tube, or alternatively, as above, the wire may be drilled to form a substantial bore in a distal end and the connector includes two male ends for fitting into the wire and into the tube.

In an alternative construction of the distalmost end of the sourcewire, a spring coil is formed at the distal end of the tube either on the plug or in combination with the welded distal end of the tube. The spring coil facilitates tracking of the sourcewire through a catheter and acts as a shock absorber to prevent the sourcewire from damaging the internal distal end of the blind lumen.

In an alternative construction and the method of forming a radioactive sourcewire, a core material is positioned within a tube and the distal end of the tube sealed by welding or with a plug as disclosed herein. A second weld or plug is provided internal to the tube adjacent the core to encapsulate the core within the tube to form a distal end assembly of a sourcewire. The distal end assembly of the sourcewire is then subject to irradiation in a nuclear reactor to render the core radioactive. After the core has been made radioactive, the distal end assembly may be affixed to a solid elongate wire in accordance with the various constructions herein.

In an alternative construction of a sourcewire, a flush proximal end of a tube is welded to a flush distal end of an elongate driving wire and an overlay tube is affixed to the outer surfaces of the proximal end of the tube and the distal end of the driving wire. Preferably, the overlay tube is affixed by means of spot welds at various locations. Additionally, an internal backbone wire may be provided in the proximal portion of the tube and secured therein by internal spot welds.

In another embodiment of the sourcewire, the sourcewire is formed by providing a flexible solid or driving wire having a predetermined outer diameter and welding a flush distal end of the driving wire to a tube having a predetermined outer diameter less than the diameter of the wire. The differences in diameters provides a natural step that, when welded, epoxyed or otherwise secured, provides a smooth tapered transition without protrusion about the juncture of the wire in the tube. Preferably, a rod extending from the distal end of the wire is configured for securement within the tube. Core material is inserted into the tube and the distal end of the tube is sealed by means of a weld or plug.

In a particular method of forming a distal end of the sourcewire, a tube is provided with a section of core material therein. The tube has an open distal end. The open distal end of the tube is welded closed with a predetermined amount of weld material to seal the distal end of the tube. Thereafter, the weld material is ground to form a tapered distal tip on the sourcewire.

BRIEF DESCRIPTION OF THE DRAWINGS

For a better understanding of the disclosure, reference is made to the following description of exemplary embodiments thereof, and to the accompanying drawings, wherein:

FIG. 1 is a partial cross-sectional view of a composite source wire including a radioactive core provided within a flexible source tube and secured therein by a plug, in accordance with the present disclosure;

FIG. 2 is an exploded partial cross-sectional view of an alternate embodiment of a source wire illustrating a solid wire on the left and a tube for housing a radioactive core on the right;

FIG. 3 is a view of the wire and tube of FIG. 2 joined together;

FIG. 12 is a side view of a source wire including a solid wire and a tube assembly welded closed on a distal end;

FIG. 13 is an exploded side view of a source wire having a radiopaque connector between a solid wire and tube;

FIG. 14 is an exploded side view of an alternative embodiment of a radiopaque connector between a solid wire and tube;

DETAILED DESCRIPTION OF PREFERRED EMBODIMENTS

Figure 4:
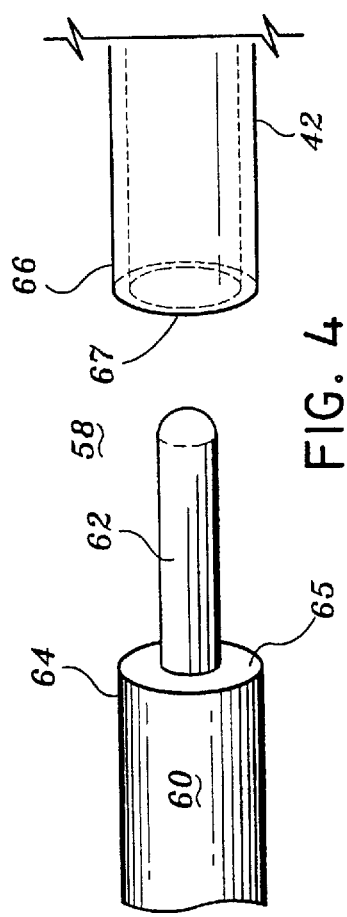
FIG. 4 is a partial cross-sectional view of an alternate embodiment of a source wire illustrating a wire having a rod secured thereto, and a tube.

Referring now to the drawings in detail, and initially to FIG. 1, a composite source wire 10 includes a thin, continuous, elongate, flexible housing tube 12 having an outer diameter and length adequate to maneuver through a tortuous narrow passage to a treatment site within the body. Housing tube 12 is preferably constructed from a material such as Nitinol®, a titanium/nickel alloy, or similar shape memory or elastic materials which exhibit little or no memory retention when the tube is bent.

A flexible backbone wire 14 is provided between a proximal end 16 of housing tube 12 and extends to several millimeters from a distal end 18 of housing tube 12. For ease of initially inserting backbone wire 14 into tube 12 and to allow greater pivoting of the assembly while reducing stress to housing material, an end 20 of wire 14 is rounded. Similar to housing tube 12, backbone wire 14 may also be constructed from material such as Nitinol®, a titanium/nickel alloy, or similar elastic materials which exhibit little or no memory retention when bent.

To assemble source wire 10, a radioactive source or core 22 is inserted into the distal end 18 of housing tube 12 until it abuts the rounded end 20 of the backbone wire 14. The rounded end 20 of the backbone wire 14 can be advantageously configured to seal the inside diameter of housing tube 12 to prevent leakage of radioactive contamination along tube 12. It is also contemplated that radioactive core 22 may be housed within its own capsule manufactured from a very thin walled metallic material, or core 22 may itself have a coating applied to an exterior surface thereof. Furthermore, the outer surface of the section of housing tube 12 surrounding radioactive core 22 is preferably plated with gold or other non-oxidizing agents to prevent oxidation. Radioactive core 22 is preferably formed of iridium 192.

A plug 24 is provided to seal distal end 18 of housing tube 12 and provide a marker visible under fluoroscopic examination. Plug 24 includes a stud portion 26 and a head portion 28. Plug 24 is inserted within distal end 18 of housing tube 12, along the dashed lines, to seal the end thereof. Plug 24 may be sealed in place using a weld, epoxy, glue, fuse or other sealing means known to one having ordinary skill in the art.

Plug 24 is preferably formed of a radiopaque material such as gold, tantalum, platinum, iridium, or other high density metal or material or any combination thereof; such that it will be visible during a fluoroscopic examination. Although not drawn to scale, plug 24 preferably has the following approximate dimensions: the length W of the stud portion 26 is approximately 0.125 inches; the width X of the stud portion 26 is approximately 0.007 inches with a tolerance of ±0.0005 inches; the length Y of the head portion 28 is approximately 0.053 inches; the width Z of the head portion 28 is approximately 0.0136 inches with a tolerance of ±0.0005 inches; and the radius R of the curvature of the head portion 28 is approximately 0.0136 inches. Plug 24 may be manufactured to other dimensions such that it is configured to fit tubes having a plurality of inside diameters and wall thicknesses, and such that it is capable of accessing a plurality of paths within the body.

Alternatively, instead of sealing distal end 18 of housing tube 12 with plug 24, the open distal end 18 may be sealed by weld material. The weld material may then be ground or machined to provide a smooth tip or smooth tapered tip, as discussed hereinbelow, for movement through the body. Also, when utilizing this alternative embodiment, a marker is preferably placed within tube 12 so that the tube may be monitored during fluoroscopic examination. The marker is preferably formed of a radiopaque material such as gold, tantalum, platinum, iridium, or other high density metal or material or any combination thereof; such that it will be visible under fluoroscopic examination.

FIGS. 2–23 represent illustrations of alternative embodiments of a composite source wire including alternative structure and methods for connecting a solid wire to a tube for housing a radioactive source, in accordance with the present disclosure. Preferably, the solid wire and tubes in the following embodiments, as well as other associated components, are formed of a material that can accept up to a 1% strain with less than a 1% permanent alteration or deformation in their respective original configurations.

Referring to FIG. 2, a composite source wire 38 is disclosed and includes a solid wire 40 to at least partially replace the hollow tube/backbone wire assembly described above with reference to FIG. 1. Many advantages will be realized when utilizing the embodiments of the source wire formed from a solid wire and tube assembly disclosed herein. For example, the source wire will be substantially less expensive to manufacture. Also, the source wire will be more resistant to breaking since the stress associated with pushing the wire through its tortuous paths will be distributed along a solid wire rather than a hollow tube. This feature will greatly increase the number of times or cycles the source wire may be safely driven. Additionally, the solid portion of the source wire will allow the source wire to be safely pushed with greater torque to help maneuver around tight bonds, thus enabling the source wire to reach more target sites within a patient's body.

A hollow tube assembly 42 is provided for housing a core or radioactive source (not shown), and is sealed at a distal end 44 thereof with a plug 46. As used herein generally, the term "radioactive source" means a core material capable of being rendered radioactive in a nuclear reactor after being assembled in the sourcewire. Plug 46 is preferably configured and dimensioned in accordance with the embodiment described above with reference to plug 24 in FIG. 1, and is similarly sealed to the distal end 44 of tube 42. Alternatively, distal end 44 may be welded closed and ground to form a smooth tip or smooth tapered tip. The solid wire 40 and the hollow tube 42 are preferably formed of Nitinol®, a titanium/nickel alloy, or other elastic materials which exhibit little or no memory retention when bent. Alternatively, as will be common throughout all embodiments herein, the tube and/or solid wire may be formed from a stainless steel alloy alone or in combination with titanium/nickel components.

FIG. 3 illustrates solid wire 40 and hollow tube assembly 42 joined together at a distal end 48 of wire 40 and a proximal end 50 of tube 42 at a location designated by numeral 52. Solid wire 40 has an end face surface 47 at distal end 48 thereof. End face surface 47 is substantially perpendicular to a longitudinal axis of solid wire 40. Similarly, hollow tube 42 includes an end face 49 which is substantially perpendicular to a longitudinal axis of hollow tube 42. Specifically, end face surface 47 (FIG. 2) of wire 40 is brought into abutment with end face surface 49 (FIG. 2) of tube 42 such that solid wire 40 may be permanently affixed or connected to hollow tube 42 in a flush face to face engagement by a circumferential weld, epoxy, glue or any other conventional means known to one having ordinary skill in the art. Preferably, the outer diameter of solid wire 40 at its distal end 48 is substantially equal to the outer diameter of hollow tube 42 at its proximal end 50. The combination of the solid wire on one side of the tube and the plug on the other side of the tube will ensure that the radioactive source will be completely encapsulated between solid ends, thus containing all radiation and any possible radioactive flakes inside a fixed cavity.

Turning now to FIG. 4, another embodiment of a composite source wire 58 in accordance with the present disclosure is illustrated wherein a solid wire 60 is illustrated having a connector or rod 62 extending from a distal end 64 thereof. Wire 60 and rod 62 are each preferably formed of Nitinol®, a titanium/nickel alloy, or other elastic materials which exhibit little or no memory retention when bent. Rod 62 may be connected to wire 60 by welding, epoxy, glue or any other suitable means, and is configured and dimensioned having an outside diameter substantially corresponding to the inside diameter of hollow tube 66 to allow a force-fit connection. Alternatively, rod 62 may be formed by grinding down distal end 64 to form an abrupt step between an outer diameter of wire 60 and rod 62. Thus, as illustrated in FIG. 5, rod 62 may be force-fit into the bore of tube 66 thereby providing additional reinforcement adjacent to the point of connecting wire 60 and tube 66.

Figure 5:
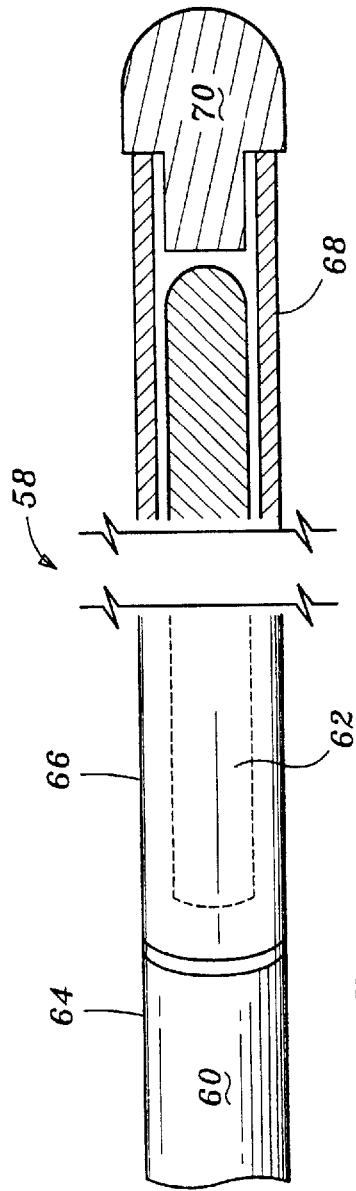
FIG. 5 is a partial cross-sectional view of the components of FIG. 4 joined together.

FIG. 5 is a partial cross-sectional view illustrating hollow tube 66 having rod 62 force-fit therein and connected to wire 60. The connection between wire 60 and tube 66 may be made by welding, epoxy, glue or any other suitable means. Specifically, to assemble sourcewire 58, an end face surface 65 (FIG. 4) of wire 60 is brought into abutment with end face surface 67 (FIG. 4) of tube 66 to facilitate the connection thereof. Although rod 62 is inserted into tube 66, each item is appropriately configured and dimensioned such that a cavity may be provided within tube 66 distal of rod 62 so that a radioactive source 68 may also be housed within tube 66. The distal end of the tube may be sealed by plug 70 to contain the radioactive source. As discussed above, it is also contemplated that plug 70 may be eliminated and the distal end of tube 66 may be sealed by weld material.

Figure 6:
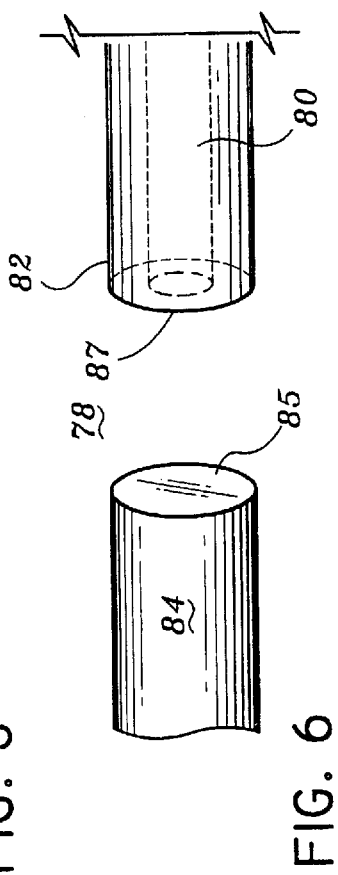
FIG. 6 is a partial cross-sectional view of an alternate embodiment of a source wire illustrating a tube having a rod therein on the right, and a wire on the left.

FIG. 6 illustrates yet another embodiment of a composite source wire 78 in accordance with the present disclosure. In FIG. 6, a rod 80, similar to rod 62 described above in FIGS. 4 and 5, is utilized to reinforce the connection between a solid wire 84 and a hollow tube 82. However, instead of first connecting the rod to the solid wire, rod 80 is first placed within tube 82 and secured therein by an interference fit, epoxy, welding or any other suitable means. Therefore, a contiguous, flush surface area is formed at a proximal end of the tube assembly to facilitate a uniform connection to solid wire 84.

Figure 7:
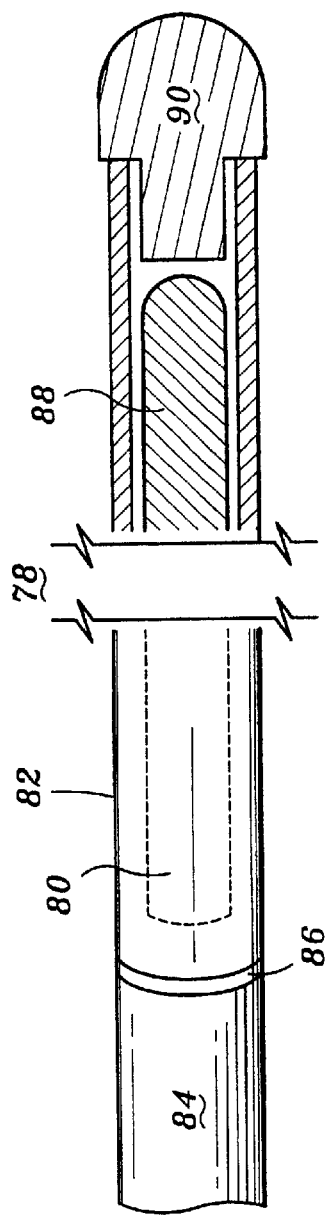
FIG. 7 is a partial cross-sectional view of the components of FIG. 6 joined together.

FIG. 7 is a partial cross-sectional view illustrating hollow tube 82 having rod 80 therein and connected to solid wire 84 by glue, epoxy, welding or any other suitable means. The connection therebetween is advantageously uniform since the contact surface area is enhanced due to the position of the rod 80 within tube 82. Specifically, an end face surface 85 (FIG. 6) of wire 84 is brought into abutment with end face surface 87 (FIG. 6) of tube 82 to facilitate the connection thereof. A circumferential or uniform weld may be made at the location indicated by numeral 86. Similar to the previous embodiments described above, a radioactive source 88 is placed within tube 82 and a plug 90 is secured within the distal end thereof to seal tube 82.

Figure 8:
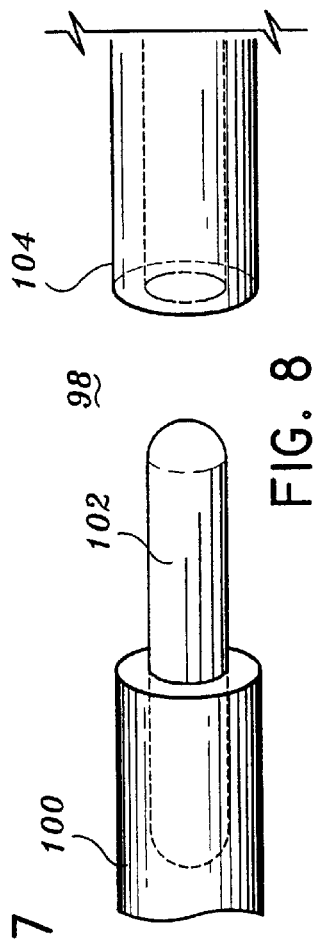
FIG. 8 is a partial cross-sectional view of an alternate embodiment of a source wire illustrating a rod partially secured within a bore in a wire on the left, and a tube on the right.

Referring now to FIG. 8, a further composite source wire 98 includes a solid wire 100 having a longitudinal bore formed at least partially therein for at least partially receiving a rod 102. The bore may be formed by drilling, laser, electric discharge machining (EDM), or any other method known to one having ordinary skill in the art. Rod 102, preferably formed of Nitinol®, a titanium/nickel alloy, or other elastic materials which exhibit little or no memory retention when bent, is secured within the longitudinal bore in solid wire 100 by an interference fit, welding, glue, epoxy or any other method known to one having ordinary skill in the art. Rod 102 is configured and dimensioned to correspond to the inside diameter of hollow tube 104. Thus, the portion of rod 102 extending from solid wire 100 may be insertably received within tube 104 and secured therein in a manner similar to that which is described above. Once rod 102 is secured within tube 104, the periphery of tube 104 may be secured to solid wire 100 by welding, glue, epoxy or any other method known to one having ordinary skill in the art.

Figure 9:
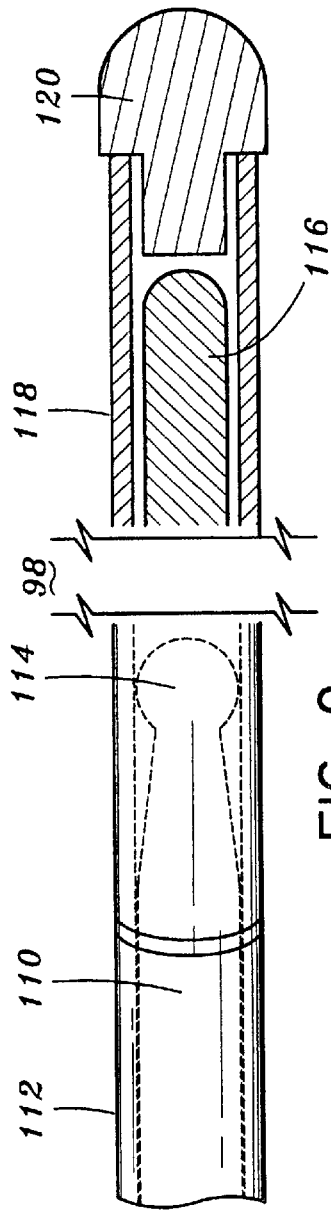
FIG. 9 is a partial cross-sectional view of an alternative embodiment of the components of FIG. 8 joined together.

FIG. 9 illustrates an alternative embodiment of a fully assembled wire/tube assembly similar to the embodiment of FIG. 8 with a variation made to the rod member to accommodate tubes having a length generally greater than 3 cm but less than 20 cm. This is necessary where the length of the treatment zone and thus of the source need be greater than about 3 centimeters. Rod 110 is connected to wire 112 in a manner similar to that which is described with reference to FIG. 8. Rod 110 also acts as a backbone wire, when the length of tube 118 exceeds 3 cm, and includes a rounded tip 114 on the distal end. The rounded tip 114 is also preferably incorporated when tube 118 is greater than 3 cm long. For tubes having a length greater than 3 cm, the length of rod 110 and the rounded tip 114 provide additional flexibility and pivoting motion of the assembly while reducing stress on the tube surface. Additionally, the taper formed adjacent rounded tip 114 will allow temporary buckling of the rod thereby enabling the tube to become even more flexible around tight bends and thus reduce the stress at critical stress points.

Rounded tip 114 is positioned to abut radioactive core 116 housed within tube 118 and is configured such that core 116 will not become wedged between the rod and the wall of the tube. Rounded tip 114 is less in diameter than the interior diameter of tube 118 or it can be substantially equal in diameter to the interior diameter of tube 118 so as to seal off radioactive core 116 proximally of rounded tip 114. The distal end of tube 118 is sealed by means of plug 120.

Figure 10:
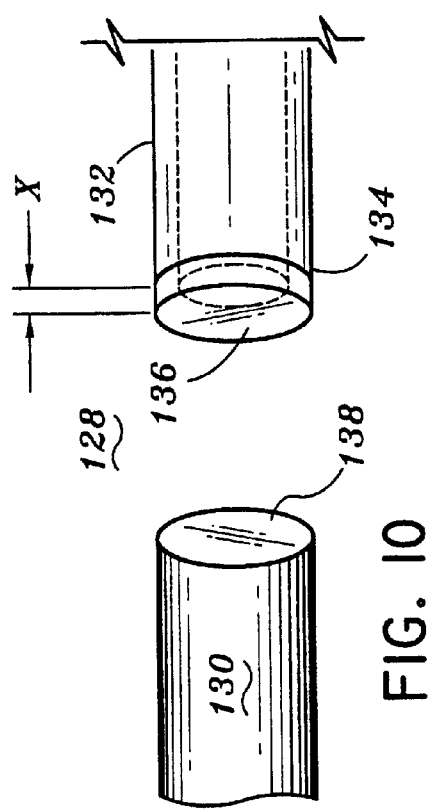
FIG. 10 is a partial cross-sectional view of an alternate embodiment of a source wire illustrating a wire on the left and a tube on the right, the tube having a welded face.

Referring now to FIG. 10, another embodiment of a composite source wire 128 in accordance with the present disclosure is illustrated having a solid wire 130 and a tube 132. Solid wire 130 and tube 132 are each preferably formed of Nitinol®, a titanium/nickel alloy, or other elastic materials which exhibit little or no memory retention when bent. The proximal end 134 of tube 132 is formed by welding tube 132 closed and grinding, or otherwise machining, the weld to form a solid, flat end face surface 136. The thickness X of end face 136 is preferably in the range of about 0.5 mm to about 2.0 mm. Advantageously, end face 136 provides additional rigidity to tube 132 such that a portion, which is slightly larger than thickness X, of tube 132 will exhibit the characteristics of a solid wire instead of a tube.

Figure 11:
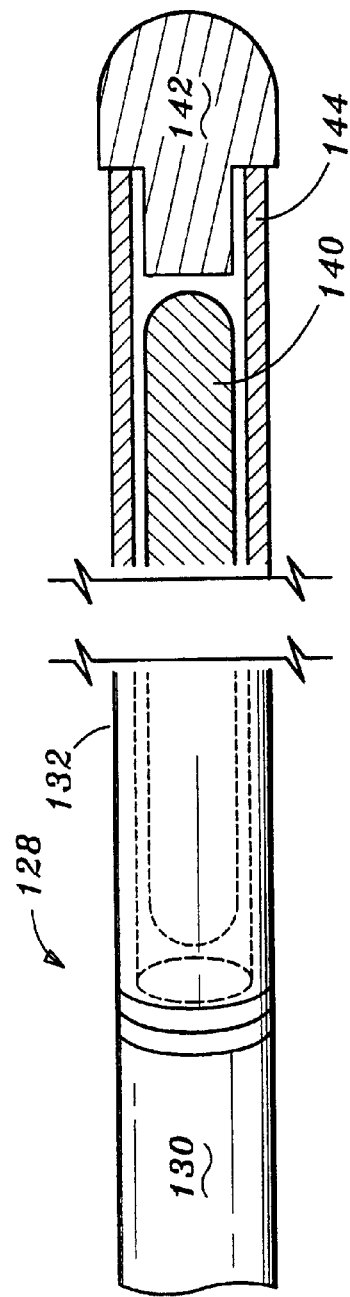
FIG. 11 is a partial cross-sectional view of an alternative embodiment of the components of FIG. 10 joined together.

As illustrated in FIG. 11, solid wire 130 and tube 132 are joined to form source wire 128. Specifically, an end face surface 138 (FIG. 10) of wire 130 is brought into abutment with end face surface 136 (FIG. 10) of tube 132 such that solid wire 130 may be connected to tube 132 by plasma welding, electron beam welding, tig welding, laser welding, epoxy, glue or any other conventional means known to one having ordinary skill in the art.

A radioactive source 140 is housed within tube 132. The combination of solid end face surface 136 on proximal end 134 of tube 132 and a plug 142 sealed within a distal end 144 of tube 132 will ensure that radioactive source 140 will be completely encapsulated between solid ends, thus containing all radiation and preventing any possible radioactive flakes from migrating out of the fixed cavity. Plug 142 is preferably configured and dimensioned in accordance with the embodiments described above, and is similarly sealed to distal end 144 of tube 132.

Referring now to FIG. 12, a further alternate embodiment of a composite source wire 158 in accordance with the present disclosure is illustrated having a solid wire 160 and a hollow tube 162 joined together, in a manner as discussed above, at location 164. Instead of sealing distal end 166 of tube 162 with a plug, the open distal end 166 may be sealed by weld material 168. The weld material may then be ground or machined to provide a smooth tip or smooth tapered tip for movement through the body. Also, when utilizing this alternative embodiment, a marker is preferably placed within tube 162 so that the tube may be monitored during fluoroscopic examination. The marker is preferably formed of a radiopaque material such as gold, tantalum or platinum, or any combination thereof; such that it will be visible under fluoroscopic examination.

FIGS. 13 and 14 illustrate alternative embodiments of a composite source wire which includes a solid wire connected to a hollow tube via a connector. The connector is preferably formed of a radiopaque material such as gold, tantalum or platinum, or any combination thereof such that the connector will be visible under fluoroscopic examination. When such materials are used to form the connector, the materials are preferably alloyed with a hardening agent, such as nickel, to prevent breakage. In FIG. 13, source wire 178 includes a solid wire 180, connector 182 and hollow tube 184. Solid wire 180 includes a rod 186 extending from a distal end thereof. Rod 186 may be welded or otherwise affixed to solid wire 180 or, alternatively, may be formed as a ground down step in solid wire 180 itself. Rod 186 is configured and dimensioned to fit within a bore 188 partially formed in a proximal end of connector 182. Similarly, connector 182 has a rod 190 extending from a distal end thereof which is configured and dimensioned to fit at least partially within a longitudinal bore 192 formed in hollow tube 184. One or more radioactive sources (not shown) are placed within bore 192 as with above embodiments. Tube 184 may be sealed at a distal end by weld material 194, or by a plug as discussed above.

Referring now to FIG. 14, a further alternative source wire 198 includes a solid wire 200, a connector 202 and a hollow tube 204. In this embodiment, connector 202 has rods 206 and 208 extending from the proximal and distal ends thereof, respectively. Rod 206 is configured and dimensioned to fit within bore 210 formed in solid wire 200, and rod 208 is configured and dimensioned to at least partially fit within a longitudinal bore 212 formed within tube 204. One or more radioactive sources are provided within tube 204. Tube 204 may be sealed at a distal end by welding material 214, or by a plug as discussed above. It is also contemplated to substitute a hollow tube for the solid wires 180, 200 FIGS. 13 and 14 respectively. Additionally, it should be noted that the above described methods of producing source wires are particularly suited to the manufacture of source wires having a wire diameter of approximately 0.012 to 0.025 inches.

Figure 15:
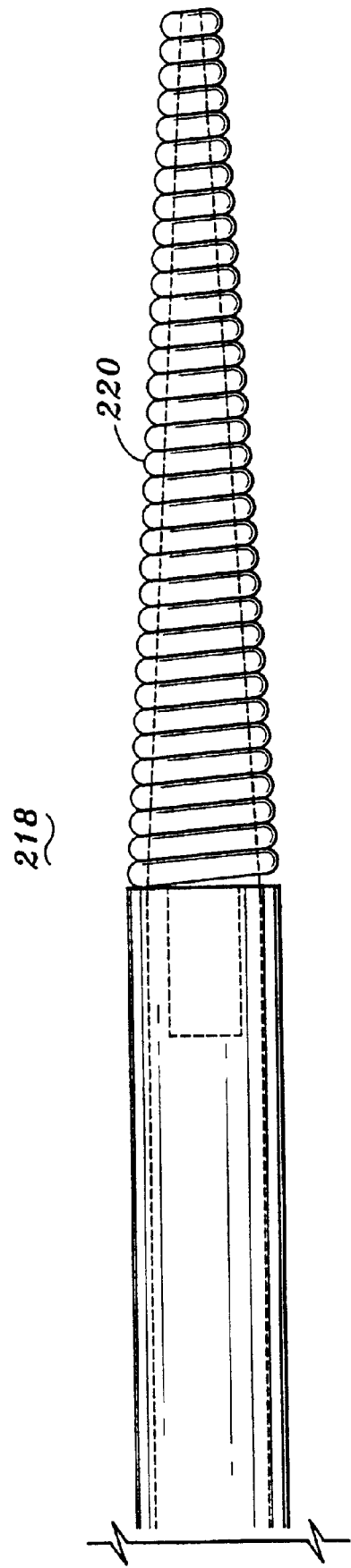
FIG. 15 is a side view of a source wire having a coil spring tip.

Referring now to FIG. 15, a composite source wire 218, formed according to the various configurations described above, is provided having a coil spring tip 220 on a distal end thereof and may be of the we, size and geometry utilized in the manufacture of guide wires. Coil spring tip 220 facilitates tracking of the source wire within a catheter and/or cushion the impact of the distal end of the source wire with the closed distal end of the catheter source wire lumen as the sourcewire is driven therein.

Figure 16:
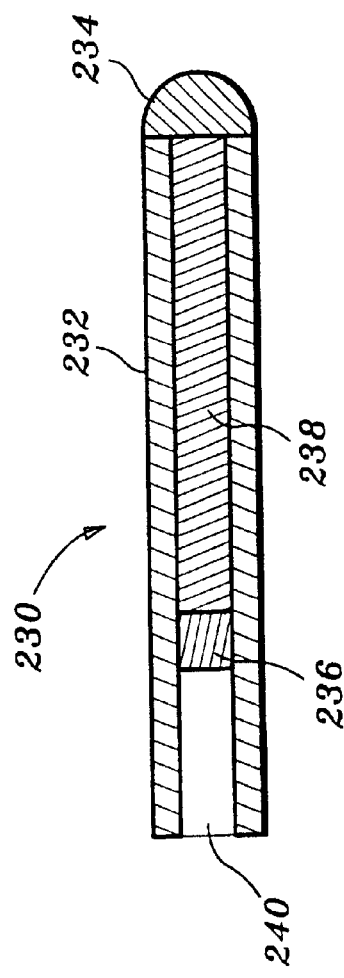
FIG. 16 is a cross-sectional view of a distal end assembly of an alternate embodiment of a sourcewire construction.

Referring now to FIG. 16, there is provided a non-radioactive distal end assembly 230 for use in forming a composite sourcewire. Distal end assembly 230 is provided to totally encapsulate a non-radioactive source inside a metal material such that several days after nuclear irradiation in a reactor only the core material remains radioactive and not the encapsulation material. This provides the advantage of forming a pre-irradiated or active source distal end without subjecting the entire sourcewire to irradiation. Distal end assembly 230 generally includes a tube 232 having a sealed or rounded distal end 234. Rounded distal end 234 may be either of the plug variety described hereinabove or it may be formed by welding the distal end of tube 232 closed and grinding or otherwise forming a smooth rounded distal end. A sealed inner plug 236 is provided within tube 232 to totally encapsulate a non-radioactive source 238 positioned within tube 232. Sealed inner plug 236 may be a solid plug welded within tube 232 or, alternatively, weld material provided within a bore of tube 232.

Once non-radioactive distal end assembly 230 has been assembled it may be taken to a nuclear reactor and subjected to irradiation. Preferably, tube 232 is formed of a material, such as, for example, titanium, so that after a few days after exiting the reactor only the core material is radioactive.

Figure 17:
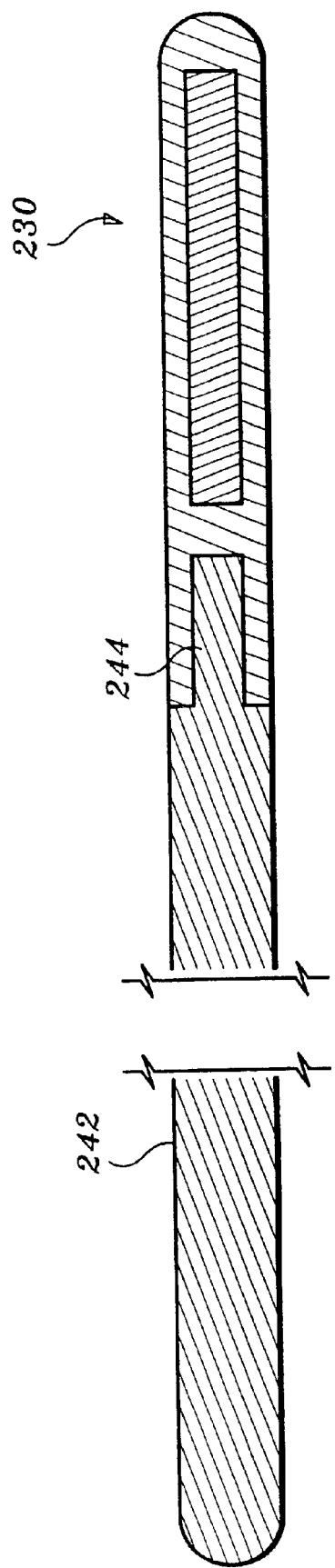
FIG. 17 is a cross-sectional view of the distal end assembly of FIG. 16 joined to a solid wire to form a sourcewire.

Referring now to FIG. 17, there is illustrated a solid wire 242 having a rod 244 extending distally therefrom. This may be formed in the manner described hereinabove. Preferably, solid wire 242 is formed of an elastic material such as, for example, a nickel titanium alloy. After distal end assembly 230 has been irradiated, rod 244 of solid wire 244 may be inserted within a bore 240 of distal end assembly 230 and welded together in a manner described hereinabove with respect to previous embodiments in order to form a composite radioactive sourcewire 248.

Figure 18:
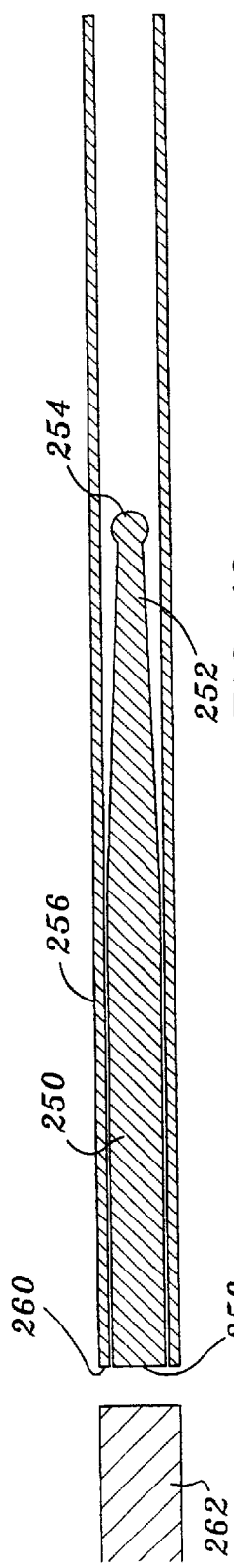
FIG. 18 is a cross-sectional view of a further alternative sourcewire prior to assembly.

Referring now to FIGS. 18–21, there is disclosed another alternate embodiment for affixing a distal end of a sourcewire to a solid, substantially elongated driving wire. Referring initially to FIG. 18, a wire 250 having a tapered distal end 252, terminating in a rounded tip 254 is provided and is inserted within a tube 256 such that a proximal end 258 of wire 250 is flush with a proximal end 260 of tube 256. Thereafter, wire 250 and tube 256 may be welded at their respective proximal ends to form a flush surface as above for mating and connection to a elongate wire 262.

Figure 19:
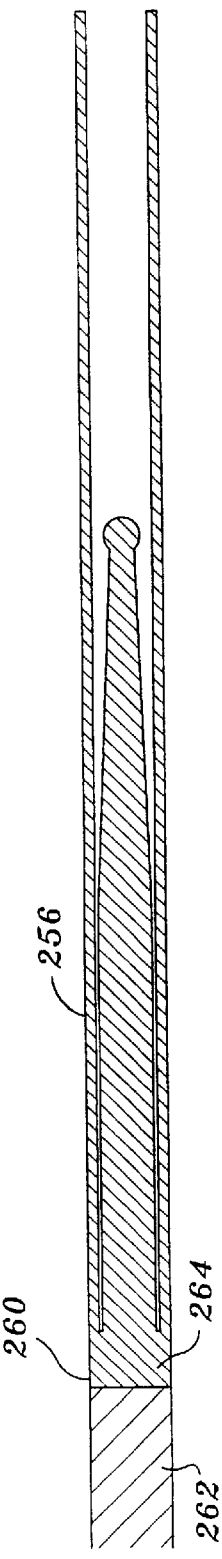
FIG. 19 is a cross-sectional view of the embodiment of FIG. 18, partially assembled.
Figure 20:
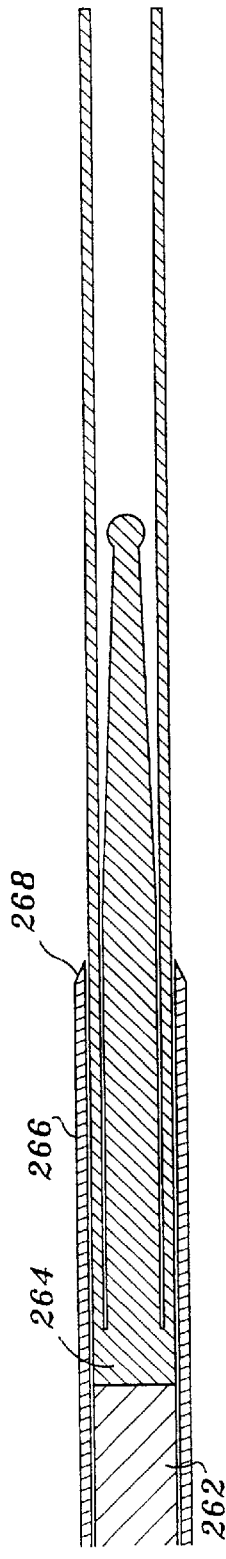
FIG. 20 is a cross-sectional view of the assembly of FIG. 19 with an outer tube overlay.

Referring to FIG. 19, wire 262 is brought into abutment with a proximal end 264 of the tube/wire assembly, formed from the welding of wire tube 250 and tube 256, and is thereafter welded, glued, epoxyed or otherwise joined similar to the manner described hereinabove.

During repeated cyclings of the sourcewire through the drum of an afterloader, this particular type joint may experience some breakdown. Therefore, referring to FIG. 20, there is also provided an overly tube 266 having a tapered distal end 268 which is configured to overly the assembly of FIG. 19. A preferred length for overly tube is approximately 1900 millimeters while a preferred distance from the distal end of overly tube 266 to the distal end of tube 256 is approximately 1350 millimeters. Wire 250 preferably has an outer diameter of 0.006 inches while tube 256 has an inner diameter of 0.007 inches and an outer diameter of 0.012 inches. Similarly, solid wire 262 has an outer diameter of 0.012 inches. Preferably, overly tube 266 has an interior diameter of 0.013 inches.

Figure 21:
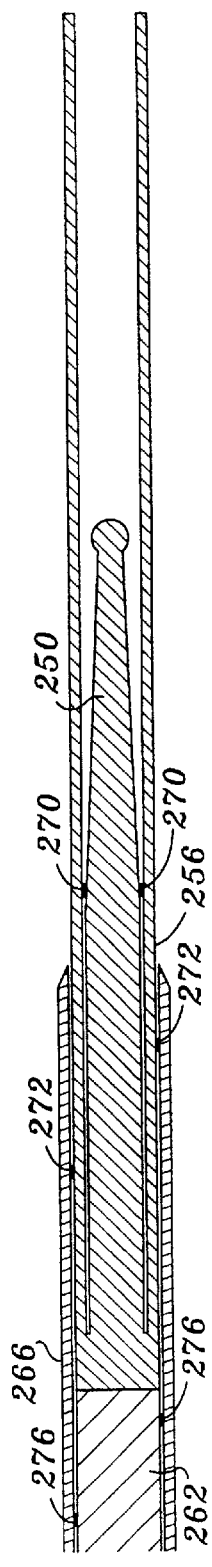
FIG. 21 is a cross-sectional view of the assembly of FIG. 20 after welding the tube overlay in place.

Referring now to FIG. 21, in order to secure the entire assembly together and provide stress release points, there are provided a series of spot welds between the various components. For example, spot welds 270 are formed between wire 250 and tube 256, spot welds 272 are formed between an exterior of tube 256 and an interior of overly tube 266 and spot welds 276 are formed between an interior of overly tube 266 and an outer surface of elongate wire 262. Once assembly has been made, the distal end of tube 256 may be provided with one or more radioactive sources and sealed or closed by means of a plug or weld as described herein.

Figure 22:
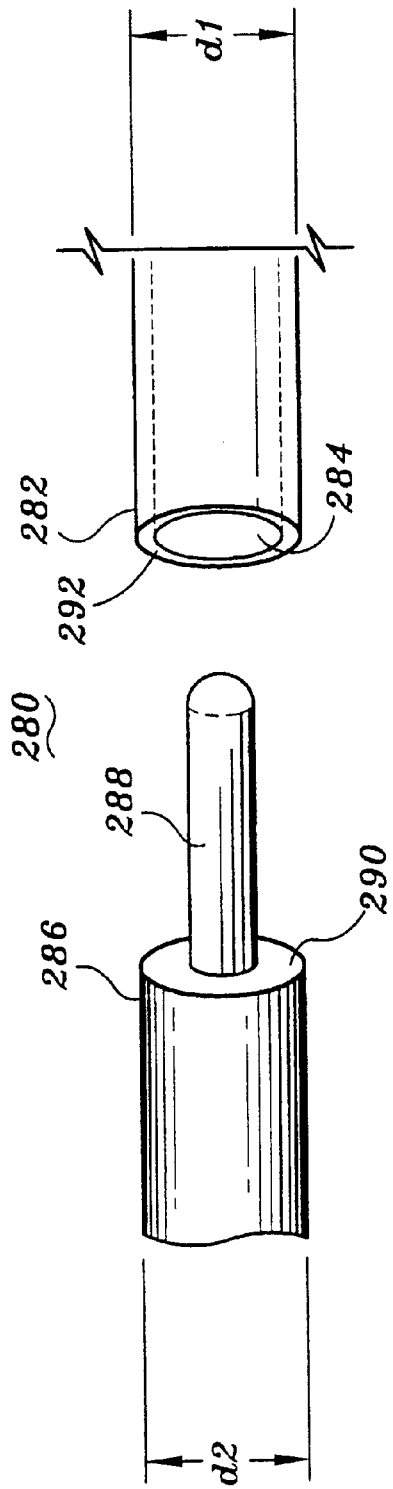
FIG. 22 is a perspective view of an alternative embodiment of a solid wire-tube connection where the diameter of the tube is smaller than the diameter of the solid wire.
Figure 23:
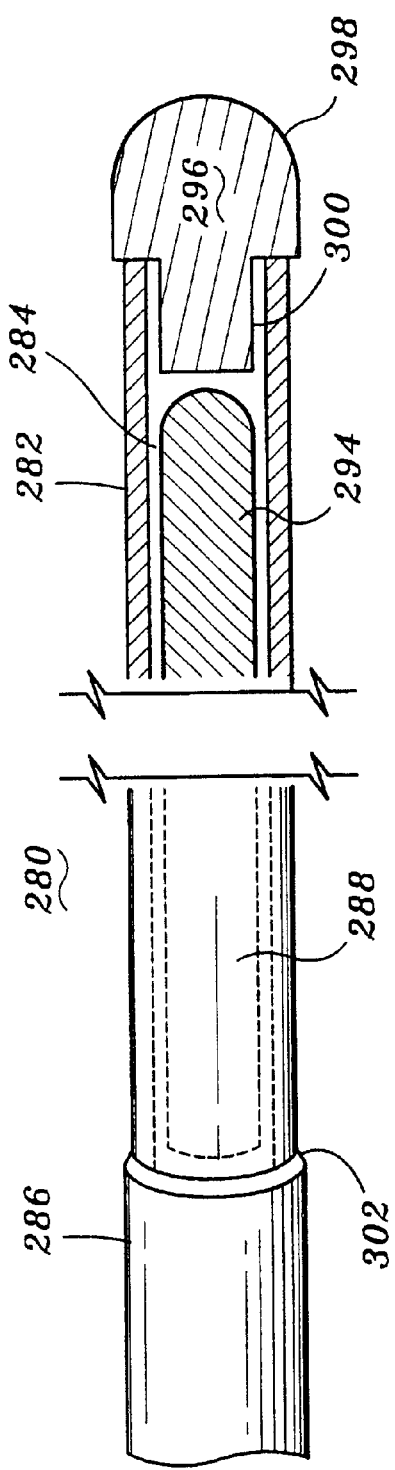
FIG. 23 is a cross-sectional view of an alternative embodiment of a sourcewire incorporating the solid wire-tube connection of FIG. 22.
Figure 24:
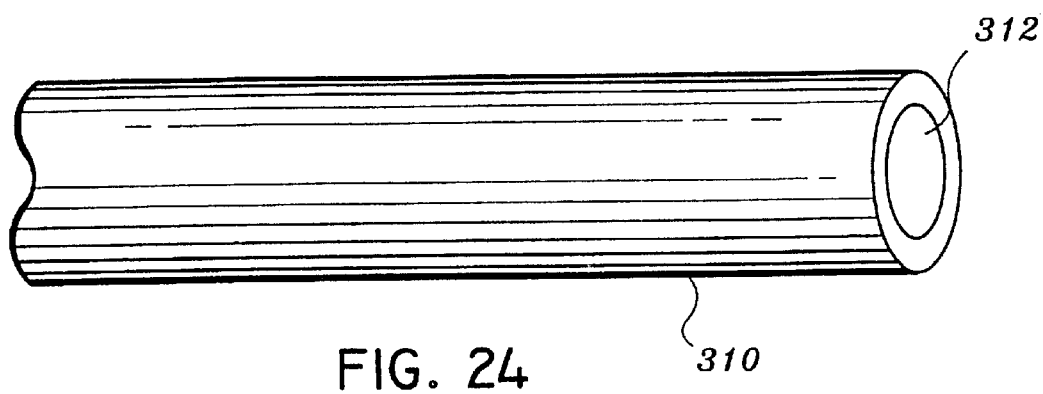
FIGS. 24–26 are perspective views of an alternative method of sealing the distal end of a tube used to retain a radioactive core in a sourcewire.

Referring now to FIGS. 22–23, there is provided an alternative sourcewire 280 and method of construction. Sourcewire 280 is constructed in a manner so as to minimize the presence of a perturbance or rough projection at the junction of a solid elongate wire and a tube welded flush thereto. This facilitates passage of the sourcewire through a treatment catheter without the possibility of snagging. Sourcewire 280 includes a tube 282 having an interior bore 284 and an elongate wire 286 having a rod 288 projecting distally therefrom. Tube 282 and wire 286 are dimensioned and configured such that when rod 288 is inserted within bore 284, a flush surface 290 of wire 286 matingly meets flush with a flush surface 292 of tube 282. Once flush surface 290 and flush surface 292 have been brought into engagement, the components may be welded and completed substantially in a manner described hereinabove with respect to FIGS. 4 and 5.

It should be noted, however, that in this embodiment tube 282 has a diameter D1, preferably of 0.010 inches whereas wire 286 has a greater diameter D2 which is preferably on the order of 0.012 inches. The 0.002 inch differential in diameter facilitates joining of the wire and tube without risking a protrusion which might inhibit trackability of the sourcewire through the delivery catheter. While a specific differential of 0.002 inches is indicated, it will be appreciated that any differential resulting in the diameter of the tube being less than the outer diameter of the wire will facilitate receipt of a weld, epoxy, etc. connection for a smooth transition.

Referring to FIG. 23, sourcewire 280 may be completed in a manner similar to that indicated above with other embodiments. Specifically, a radioactive source 294 may be inserted within tube 282 and tube 282 will be sealed at a distal end by means of a plug 296. Plug 296 preferably has a rounded distal end 298 and a stud 300 extending proximally for insertion within bore 284 of tube 282. Alternatively, distal end of tube 282 may be welded shut and ground as described herein with respect to other embodiments. Depending on the method used to secure tube 282 to wire 286, for example, welding, such as laser welding, tig welding, or epoxying, there will result a relatively smooth snag free junction 302.

Figure 25:
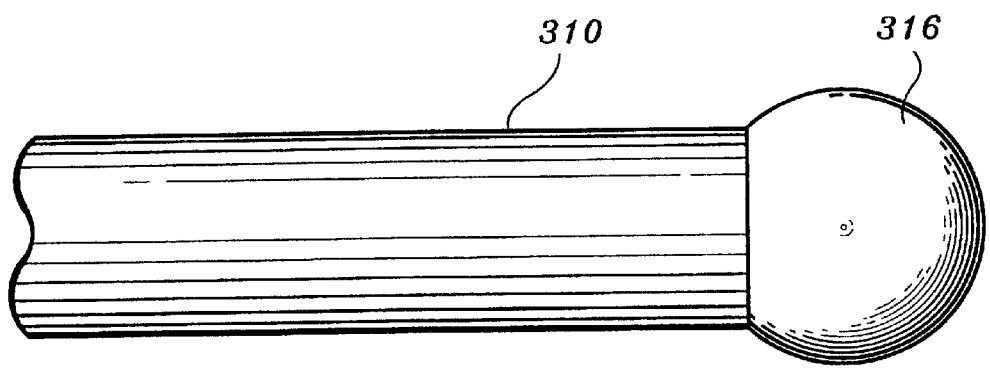
Figure 26:
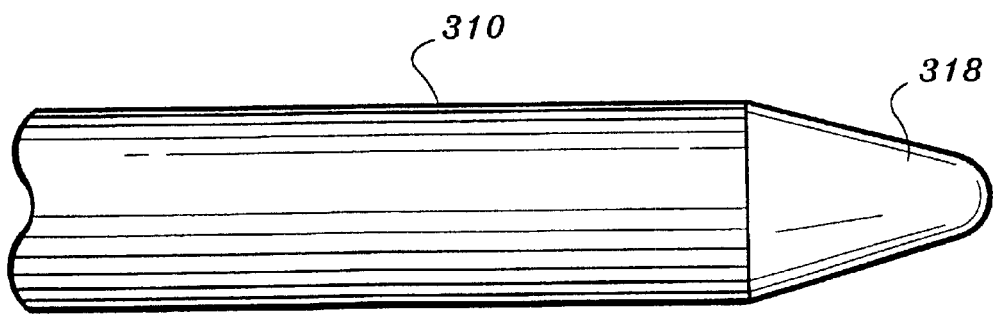
Figure 27:
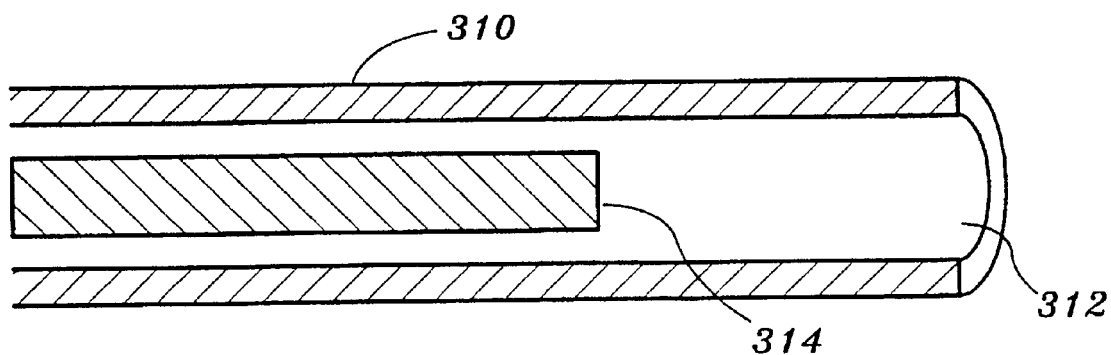
FIGS. 27–29 are cross-sectional views corresponding to the sealing method of FIGS. 24–26, respectively.
Figure 28:
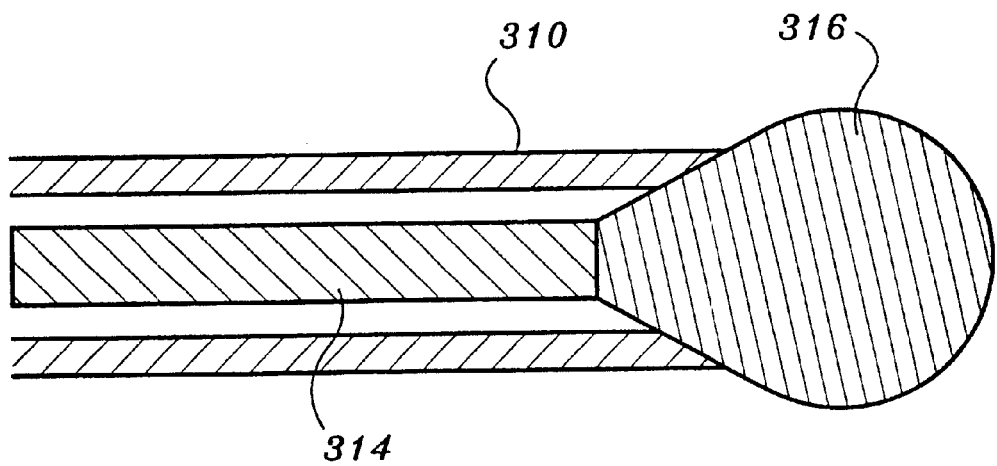
Figure 29:
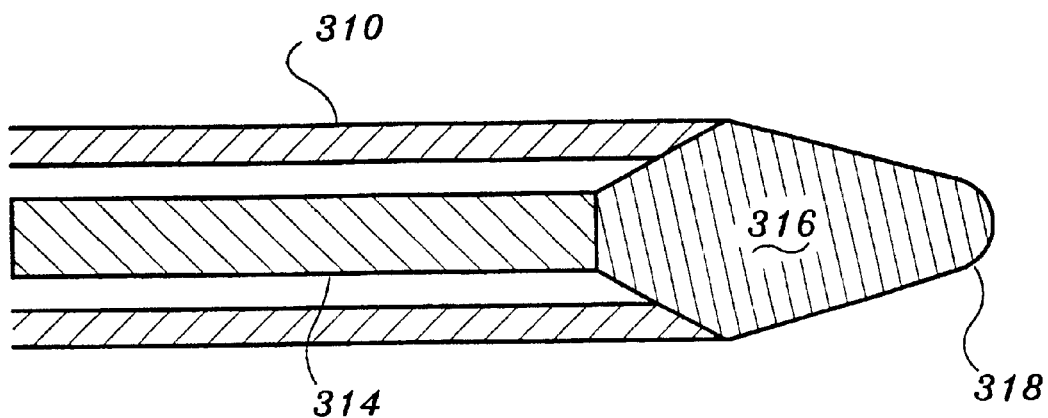

Referring now to FIGS. 24–29, there is disclosed an alternative method of sealing a distal end of a tube containing a radioactive core. Specifically, referring to FIGS. 24 and 27, there is provided a tube 310 having an interior bore 312 for receipt of at least one radioactive source or core 314. Referring to FIGS. 25 and 28, in this method, the distal end of tube 310 is welded shut with a suitable amount of weld material to form a plug 316 extending into bore 312 and adjacent core 314 to seal distal end of tube 310. Once distal end 310 has been sealed with plug 316, plug 316 as best shown in FIGS. 26 and 29, may be then ground down or otherwise treated to form a tapered distally projecting surface 318 of plug 316.

Additional advantages and features generally attributable to the embodiments of a source wire/tube assembly for radiation treatment as disclosed herein and described above, include a source wire which will be easier to maneuver since a solid wire is more resistant to buckling or kinking than the conventional tube assembly. Also, a natural taper associated with the smaller diameter tube connected to the larger diameter solid wire will enable the end of the source wire/tube assembly to be more flexible and will minimize the possibility of the source wire becoming caught within the applicator or afterloader while in transit. The source wire may be driven with more force or torque through its tortuous path since, in the embodiments described above, a solid source wire is backing the tube section instead of merely providing support within an elongate tube.

It will be understood that various modifications may be made to the disclosed embodiments. For example, stainless steel may be substituted for any or all of the materials used to form the tube, driving wire, connecting rods or connectors and/or distal plug. Thus, the above description should not be construed as limiting but merely as exemplifications of preferred embodiments. Those skilled in the art will envision other modifications within the scope of the claims appended hereto.

What is claimed is:

1. A sourcewire for radiation treatment of diseases comprising:
   a relatively long elongate flexible wire having a proximal end and a distal end, the distal end of the wire having a wire end face substantially perpendicular to a longitudinal axis of the wire;
   a relatively short flexible tube having a proximal end and a distal end, the distal end of the tube being sealed, the tube having a tube end face at the proximal end and substantially perpendicular to a longitudinal axis of the tube, the proximal tube end face being fixedly attached to the distal wire end face of the wire, the tube having an inner diameter defining a cavity; and
   a core capable of being irradiated to form at least one radioactive source positioned within the cavity.

2. The sourcewire as recited in claim 1, wherein an outer diameter of the wire and an outer diameter of the tube are substantially equal.

3. The sourcewire as recited in claim 1, further comprising a connector extending distally from the wire end face, the connector extending at least partially into the cavity of the tube.

4. The sourcewire as recited in claim 3, wherein a proximal end of the connector is affixed to the wire end face.

5. The sourcewire as recited in claim 3, wherein the connector extends distally out of a bore formed in the wire end face.

6. The sourcewire as recited in claim 1, further comprising a connector positioned in the cavity of the tube such that a proximal end face of the connector is flush with the tube end face.

7. The sourcewire as recited in claim 1, wherein the tube end face is a solid flat end face, the solid flat end face being affixed to the wire end face.

8. The sourcewire as recited in claim 1 wherein the wire and the tube are formed of a nickel/titanium alloy.

9. The sourcewire as recited in claim 1, wherein the sealed distal end of the tube includes a plug at least partially positioned within the cavity.

10. The sourcewire as recited in claim 1, wherein the outer diameter of the distal end of the flexible wire is greater than the outer diameter of the proximal end of the tube.

11. The sourcewire as recited in claim 1, wherein the wire and the tube are formed of a material that can accept up to a 1% strain with less than a 1% permanent alteration in the sourcewires original configuration.

12. The sourcewire as recited in claim 1, wherein at least one of the tube or flexible wire is formed from a stainless steel alloy.

13. The sourcewire as recited in claim 1, further comprising a coiled spring tip extending distally from the sealed distal end of the tube.

14. The sourcewire as recited in claim 1, wherein the sealed distal end of the tube forms a tapered tip.

15. The sourcewire as recited in claim 1, further comprising an overlay tube affixed to outer surfaces of the distal end of the wire and a proximal end of the tube.

16. A method of forming a sourcewire for radiation treatment of diseases comprising the steps of:
   providing a relatively long flexible wire having a wire end face substantially perpendicular to a longitudinal axis of the wire,
   a relatively short flexible tube having a proximal end and a distal end, an inner diameter and an outer diameter, the inner diameter of the tube forming a cavity, the proximal end of the tube having an tube end face substantially perpendicular to a longitudinal axis of the tube, and
   a core capable of being irradiated to form at least one radioactive source dimensioned to fit within the inner diameter of the tube;
   permanently affixing the wire end face of the wire flush with the tube end face of the tube;
   inserting at least one radioactive source within the cavity; and
   sealing the distal end of the tube.

17. The method as recited in claim 16, wherein the step of permanently affixing includes welding, gluing, and/or epoxying the tube end face flush to the wire end face.

18. The method as recited in claim 16, further comprising the step of forming a connector extending from the wire end face and inserting a distal end of the connector into the cavity.

19. The method as recited in claim 18, wherein the step of forming includes grinding a distal end of the wire to form the connector extending from the wire end face.

20. The method as recited in claim 18 wherein the step of forming includes welding, gluing and/or epoxying a rod to the wire end face.

21. The method as recited in claim 18, further comprising the step of forming a bore within the distal end of the wire and inserting the proximal end of the connector within the bore.

22. The method as recited in claim 16, further comprising the step of forming the tube end face by welding the proximal end of the tube closed end forming a flush surface to form the tube end face.

* * * * *